United States Patent
Meron et al.

(10) Patent No.: US 11,726,020 B2
(45) Date of Patent: Aug. 15, 2023

(54) METHOD AND SYSTEM FOR INSTALLING WATER POTENTIAL DETECTORS IN PLANT STEMS, AND FOR EVALUATING PLANT IRRIGATION CONDITIONS

(71) Applicant: Saturas Ltd., Misgav Industrial Park (IL)

(72) Inventors: Moshe Meron, Misgav Industrial Park (IL); Erez Sokolsky, Misgav Industrial Park (IL); Avishai Avni, Misgav Industrial Park (IL); Anat Halgoa Solomon, Misgav Industrial Park (IL); Yossi Gross, Misgav Industrial Park (IL)

(73) Assignee: Saturas Ltd., Misgav Industrial Park (IL)

( * ) Notice: Subject to any disclaimer, the term of this patent is extended or adjusted under 35 U.S.C. 154(b) by 819 days.

(21) Appl. No.: 16/607,444

(22) PCT Filed: Apr. 26, 2018

(86) PCT No.: PCT/IL2018/050465
§ 371 (c)(1),
(2) Date: Oct. 23, 2019

(87) PCT Pub. No.: WO2018/198125
PCT Pub. Date: Nov. 1, 2018

(65) Prior Publication Data
US 2020/0141851 A1 May 7, 2020

Related U.S. Application Data

(60) Provisional application No. 62/491,336, filed on Apr. 28, 2017.

(51) Int. Cl.
| | |
|---|---|
| *G01N 13/04* | (2006.01) |
| *A01G 7/06* | (2006.01) |
| *A01G 25/16* | (2006.01) |
| *G01N 7/10* | (2006.01) |
| *G01N 33/00* | (2006.01) |
| *A01G 22/00* | (2018.01) |

(52) U.S. Cl.
CPC ............... *G01N 13/04* (2013.01); *A01G 7/06* (2013.01); *A01G 25/16* (2013.01); *G01N 7/10* (2013.01);
(Continued)

(58) Field of Classification Search
None
See application file for complete search history.

(56) References Cited

U.S. PATENT DOCUMENTS

| | | |
|---|---|---|
| 4,176,495 A | 12/1979 | Dale |
| 5,467,271 A | 11/1995 | Abel et al. |

(Continued)

FOREIGN PATENT DOCUMENTS

| | | |
|---|---|---|
| CN | 106030280 A | 10/2016 |
| CN | 106234050 A | 12/2016 |

(Continued)

OTHER PUBLICATIONS

Anat Halgoa Solomon, "Advanced Sensor for Optimal Irrigation", Saturas Precision Irrigation, 5th Annual Trendlines Company Showcase, Jan. 2015, www.youtube.com/watch?v=BQRFw8IXafk (Year: 2015).*

(Continued)

*Primary Examiner* — Paul B Yanchus, III
(74) *Attorney, Agent, or Firm* — Marshall, Gerstein & Borun LLP

(57) ABSTRACT

The present invention provides devices, systems and methods for installing water potential detectors in plants stems, measuring the water potential in the plants, and evaluating crop irrigation conditions.

18 Claims, 12 Drawing Sheets

(52) U.S. Cl.
CPC ......... *G01N 33/0098* (2013.01); *A01G 22/00* (2018.02)

(56) References Cited

U.S. PATENT DOCUMENTS

| | | | |
|---|---|---|---|
| 8,695,407 B2 | 4/2014 | Stroock et al. | |
| 2012/0079876 A1 | 4/2012 | Stroock et al. | |
| 2015/0096081 A1* | 4/2015 | Jevsnik | A01G 29/00 800/298 |
| 2016/0327536 A1 | 11/2016 | Meron | |
| 2018/0129175 A1* | 5/2018 | Jennings | G06V 20/188 |

FOREIGN PATENT DOCUMENTS

| | | | |
|---|---|---|---|
| WO | WO-9804915 A1 * | 2/1998 | ........... A01G 25/167 |
| WO | 2014201442 | 12/2014 | |
| WO | 2016185477 | 11/2016 | |

OTHER PUBLICATIONS

International Application No. PCT/IL2018/050465, International Search Report and Written Opinion, dated Aug. 2, 2018.

Dixon et al., A new stem hygrometer, corrected for temperature gradients and calibrated against the pressure bomb, Plant, Cell & Environment, vol. 7. Issue 9. pp. 693-697 (1984).

Legge et al., Hydraulic Characteristics of Mountain Ash (*Eucalyptus regnans* F. Muell.) Derived From in situ Measurements of Stem Water Potential, Australian Journal of Plant Physiology 12(1) pp. 77-88 (1985). [Abstract Only].

McBurnay et al., The Relationship between Stem Diameter and Water Potentials in Stems of Young Cabbage Plants, Journal of Experimental Botany, vol. 35, Issue 12, pp. 1787-1793 (1984). [Abstract Only].

\* cited by examiner

```
┌─────────────────────────────────────────────────────────────────────┐
│ providing a water potential detector having a pressure sensor   11  │
└─────────────────────────────────────────────────────────────────────┘
                                    │
                                    ▼
┌─────────────────────────────────────────────────────────────────────┐
│ maintaining the one or more selective barrier of the water potential│
│ detector wet throughout the delivery thereof to the plant site and 12│
│ throughout its installation in the plant stem                       │
└─────────────────────────────────────────────────────────────────────┘
                                    │
                                    ▼
┌─────────────────────────────────────────────────────────────────────┐
│ forming a bore through the plant stem                            13 │
└─────────────────────────────────────────────────────────────────────┘
                                    │
                                    ▼
┌─────────────────────────────────────────────────────────────────────┐
│ (optional) smoothening the inner walls of the bore               14 │
└─────────────────────────────────────────────────────────────────────┘
                                    │
                                    ▼
┌─────────────────────────────────────────────────────────────────────┐
│ inserting the water potential detector into the bore             15 │
└─────────────────────────────────────────────────────────────────────┘
                                    │
                                    ▼
┌─────────────────────────────────────────────────────────────────────┐
│ filling gaps between the water potential detector and the stem tissue 16│
└─────────────────────────────────────────────────────────────────────┘
                                    │
                                    ▼
┌─────────────────────────────────────────────────────────────────────┐
│ (optional) connecting each detector to a controller and operating 17│
│ thereof.                                                            │
└─────────────────────────────────────────────────────────────────────┘
                                    │
                                    ▼
┌─────────────────────────────────────────────────────────────────────┐
│ (optional) fastening said water potential detector in place      18 │
└─────────────────────────────────────────────────────────────────────┘
```

Fig. 3

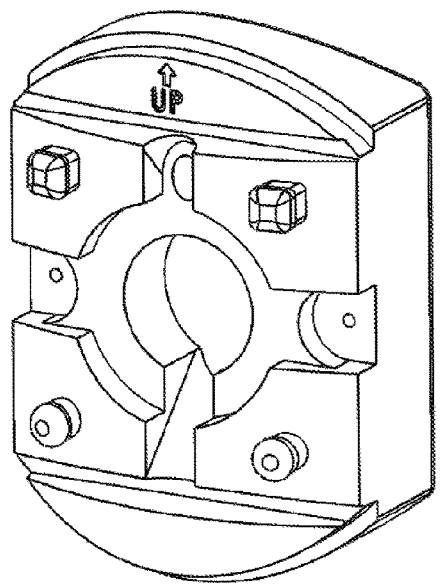
Fig. 6B
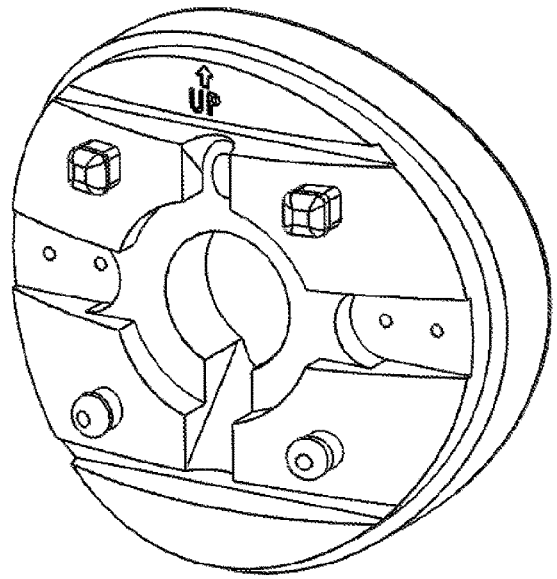
401
Fig. 6A
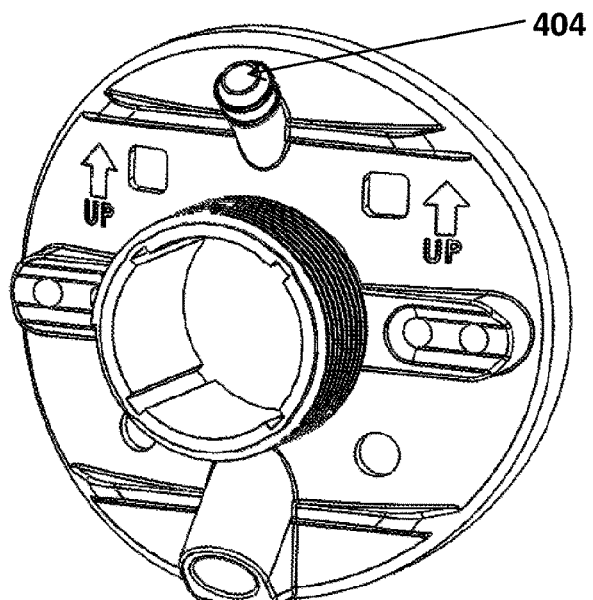
402
403  Fig. 6C

METHOD AND SYSTEM FOR INSTALLING WATER POTENTIAL DETECTORS IN PLANT STEMS, AND FOR EVALUATING PLANT IRRIGATION CONDITIONS

FIELD OF THE INVENTION

The present invention generally relates to devices, apparatuses, systems and methods for measuring water potentials in plants and evaluating crop irrigation condition. More particularly, the present invention provides devices, apparatuses, osmometers, detectors, systems and methods, for installing water potential detectors in plants stems.

BACKGROUND OF THE INVENTION

Water potential in plants is a key measurement for determining the water activity in a living plant. Measured water potential in plants is expressed in pressure units, with negative magnitudes, and from about −0.3 MPa (MegaPascal) at the roots, through about −1 MPa in the stem and about −2 MPa at the canopy and towards about −100 MPa in the atmosphere. As water flow from high potential to low potential, so does water in plants flow from the soil, into the roots, and via the stem and canopy to the atmosphere. Accurate measurement of plant water potential is essential information for determination of irrigation state of the crop. Thus, continuous monitoring of water potential in crops is key factor for determination of the optimal irrigation in precision agriculture.

Connecting measuring devices into the xylem vessels disrupts the soil-plant-atmosphere water continuum. Accordingly, measuring apoplastic (inter cellular tissue space) water potentials of abraded stem tissue by psychrometry has been developed (McBurney and Costigan, 1984; and Dixon and Tyree, 1984). However, the rigorous operational requirements of this instrument limit its use to scientific applications, whereas the device is not suitable for practical farming.

U.S. Pat. No. 8,695,407 provides a MEMS device for water potential measurement, in which a probe is inserted into the stem and measures the water potential via the vapor phase.

Various methods and systems are currently used in the agricultural industry for measuring various parameters indicative of water stress in crops for improving crop irrigation.

Some of these systems include infrared (IR) based thermal mapping for measuring water stress in the plants of the crop. This mapping requires placing one or more thermal imaging devices (e.g. IR cameras) in the field(s), calibrating the devices, and acquiring thermal images of the crop, while comparing with reference temperature measurement (e.g. obtained by using a thermometer). Usually, to deduce the water stress from the thermal image of the crop, a temperature index (Crop Water Stress Index (CWSI)) is used to calibrate the measured data from the IR camera.

Water potentials in plants are historically measured with a pressure chamber into which a cut leaf is inserted while the petiole protrudes out, applying pressure to the leaf, and reading the equilibrium pressure value when a drop of the extruded sap is shown at the petiole. It has been shown that water potential, measured from wrapped leaf isolated from transpiration and equilibrated with the stem water potential (SWP) is the best integration of the overall water continuum potentials from the soil, through the plant and up to the atmosphere, therefore the best representation of the water potential of the tree.

To actually measure the water potential inside the plants of the crop, at least a reasonable amount of plants in the crop must be equipped with a water potential sensor. Some of these sensors or detectors requiring insertion thereof into the plant stem, whereas others measure water potential on and/or in the ground near the plant stem.

One method for inserting a water potential sensor into a plant's stem is described in Legge et al. (Aust. J. Plant Physiol., 1985, Vol. 12: 77-88), which inserted an osmotic tensiometer into a tree by hammering a hole in the bark and filling it with water above the punch level to keep the tissue in the hole wetted; installing the senor in the hole; and filling the hole with caulking compound.

Variable-rate irrigation by machines or solid set systems has become technically feasible. However, mapping crop water status is still necessary to match irrigation quantities to site-specific crop water demands. Accordingly, the present invention provides devices, systems and methods for meeting this need, while overcoming most of the disadvantages of the known techniques.

SUMMARY OF THE INVENTION

In one aspect, the present invention provides a method for installing a water potential detector in a plant stem comprising the steps of: (a) providing a water potential detector comprising: (i) a compartment with an osmoticum therein; (ii) at least one selective barrier for selective transfer of water between the plant tissue and the osmoticum, while blocking transfer of other ingredients within the plant fluid; (iii) a pressure sensor configured for sensing changes in pressure of said osmoticum in said compartment, wherein said water potential detector being configured for measuring water potential through intermediate contact with plant tissue adjacent to the vascular conduit of said plant stem via said at least one selective barrier; and (iv) optionally, a temperature sensor for measuring the temperature: inside the plant stem, of the sensor, or of the environment, or all; (b) forming a bore through the plant stem by drilling therein; (c) optionally, smoothening the inner walls of the bore; (d) inserting said water potential detector into the smoothened bore while placing a conductive gel in between said at least one selective barrier and the stem tissue of the plant, such that there is no direct contact between said at least one selective barrier and the stem tissue of the plant; (e) maintaining the stem tissue in the bore wet throughout the installation process; and (f) filling any remaining gaps between said water potential detector and the stem tissue with a fluid conducting material.

In another aspect, the present invention provides a method for measuring fluid potential in a plant tissue, said method comprising the steps of: (a) installing a water potential detector in a plant stem according to the method of the invention, such that it creates hydraulic continuum with the plant tissue; (b) sensing changes in pressure caused due to osmosis based on flow of water into or out of said compartment caused to equilibrate the chemical potential of the plant tissue fluid and the osmoticum within the compartment; (c) sensing the temperature inside the plant tissue or the environment, or both; and (d) outputting electrical signal indicative of the sensed pressure, said changes are related to the fluid potential of the plant tissue with correlation to the environment temperature.

In yet another aspect, the present invention provides a system for measuring fluid potential and evaluating irrigation condition in a group of plants, said system comprising: (a) a multiplicity of water potential detectors as defined above, each detector is to be inserted into a different plant of said group of plants according to the method of the invention; (b) at least one temperature sensor, either as part of said water potential detectors, or as an independent sensor, or both; and (c) a central unit configured for: (i) receiving sensor data from said pressure and temperature sensors within, optionally in real time, (ii) calculating the fluid potential of each plant in the group of plants based on data obtained from the sensors within said detectors, (iii) calculating the irrigation condition of each plant in the group of plants and/or of the entire group, according to the calculated fluid potential of each plant; and (iv) presenting the calculated fluid potential and/or irrigation condition of each plant and/or of the entire group of plants.

The present invention also provides a system for evaluating irrigation condition in crops using thermal imagery, comprising: (a) at least one thermal imagery system configured for thermal mapping of an area; (b) at least one water potential detector as defined herein configured for measuring water potential in a plant stem in which it is installed and transmitting data indicative of its measurements; and (c) a central unit configured for receiving thermal imaging data indicative of acquired crop temperature maps, receiving data from the at least one water potential detector and for processing the received data for evaluating irrigation condition of the crop using the data from the at least one water potential detector reference for calibrating the data from the thermal imagery system.

According to some embodiments, each thermal imagery system comprises at least one thermal imaging camera e.g. based on infrared (IR) imaging.

The present invention further provides a method for evaluating irrigation condition in crops using thermal imagery comprising: (a) receiving data from at least one thermal imagery system configured and positioned for thermal mapping of the crop area; (b) receiving data from at least one water potential detector installed in a plant stem according to the installation method of the invention, indicative of water potential of the plant stem; (c) calibrating the thermal data from the at least one thermal imagery system by using the received data from the water potential detectors; and (d) evaluating irrigation condition of the crop based on the calibration data.

In some embodiments, the evaluation of the irrigation condition of the crop is carried out by also using the water potential data received from the at least one water potential detector.

The present invention further provides a method for calibrating data from a thermal imagery system for irrigation condition detection in a crop comprising: receiving data from a thermal imagery system configured and positioned for thermal mapping of a crop area; receiving data from at least one water potential detector installed in a plant stem in a plant of the crop, indicative of water potential of the plant stem; and calibrating the thermal data from the at least one thermal imagery system by using the received data from the water potential detectors.

BRIEF DESCRIPTION OF THE DRAWINGS

FIG. 1A is an upper view; and FIG. 1B is a side view.

FIG. 2A is when the device was installed by known technique; and FIG. 2B is when the device was installed according to the method of the invention.

FIG. 3 is a flow chart illustrating an exemplary method of the invention for installing a fluid-potential measuring device in a plant's stem.

FIGS. 6A-6B are pictures of a drilling and fastening means according to one embodiment of the invention: FIGS. 6A-6B illustrate two possible configurations of a base unit/pad that is attached to a tree bark at the drilling location; FIG. 6C is a cover unit/front panel that is attached to the base unit.

FIG. 7A is an explosion view; and FIG. 7B is a cross-section view.

FIG. 8A is an explosion view; and FIG. 8B is a cross-section view.

DETAILED DESCRIPTION OF SOME EMBODIMENTS OF THE INVENTION

Figures 1A, 1B:
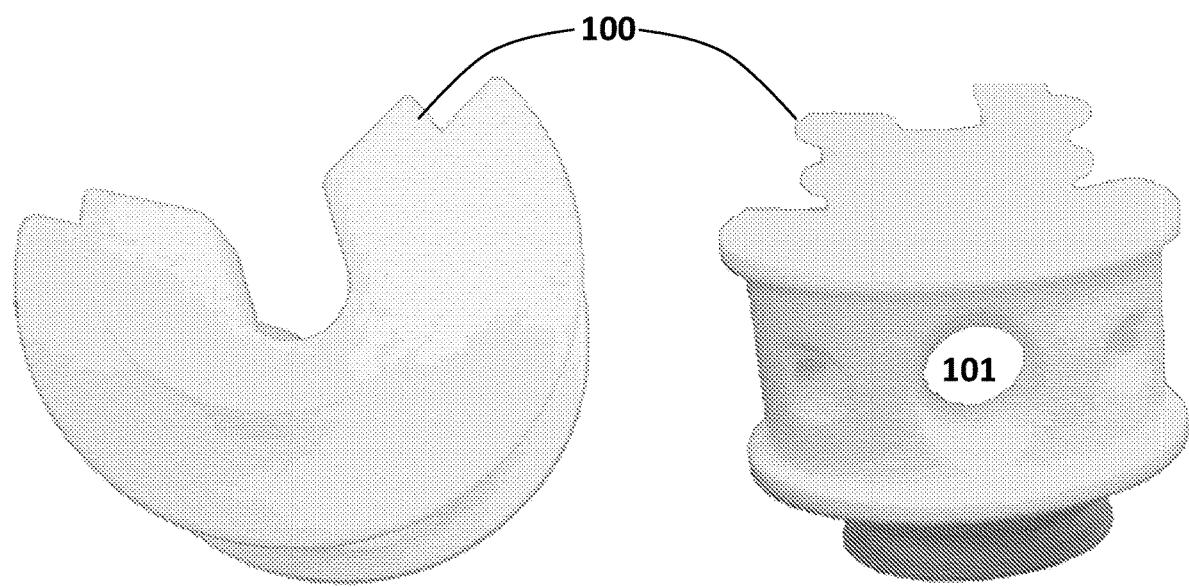
FIGS. 1A-1B are pictures of an exemplary fastening means for securing a fluid-potential measuring device without damaging the plant's stem.

Knowing the real hydration condition of plants and crops is of the upmost importance in the agricultural field. It can reduce irrigation costs as it enables to determine when a plant actually needs water, prevent over-irrigation which might damage the plants and incur additional costs, and prevent dehydration of plants due to insufficient irrigation. Accordingly, many devices, methods and systems have been developed to measure the actual water potential within a plant at a given time.

The present invention provides such methods, devices and systems for measuring real-time water potential in a given plant.

The present invention provides fluid potential measuring devices, systems and methods of installing same in a plant's stem. The present invention further provides systems comprising multiple such water potential measuring devices that can monitor and optionally also control irrigation status of one or more groups of plants in which each plant or some of the plants have a measuring device installed therein.

According to some embodiments, the measuring device used according to the method and system of the invention is configured for measuring stem water potential (SWP) via fluid-to-fluid contact and therefore requires the bore to be adjacent to the stem vascular conduit. To allow such fluid-to-fluid contact, the detector has a compartment with an osmoticum, such as PEG, therein; at least one selective barrier for selective transfer of fluids between the plant tissue and the osmoticum, such as a membrane; and a pressure sensor configured for detecting changes in pressure of fluid in said compartment, wherein the water potential detector is configured for measuring water potential through contact/interaction between the osmoticum in the compartment and the plant tissue adjacent to the vascular conduit of the plant stem via said at least one selective barrier.

It should be noted that the skilled artisan would clearly understand that when reference is made to "at least one selective barrier for selective transfer of fluids between the plant tissue and the osmoticum", at least two, three, four or more selective barrier layers can be used. Said selective barrier layers can either be the same or different, each having different properties and purposes. For instance, two selective barrier layers can be used, one is a membrane and the other is a rigid porous structure externally covering said membrane.

In a specific embodiment, the measuring device of the invention comprises a single selective barrier for selective transfer of fluids between the plant tissue and the osmoticum.

In another specific embodiment, the measuring device of the invention comprises at least two selective barriers. In a more specific embodiment, one selective barrier layer of said at least two selective barrier layers is a membrane selected from a reverse osmosis (RO) membrane, forward osmosis (FO) membrane or a Nano filtration (NF) membrane; and another selective barrier layer of said at least two selective barrier layers is a rigid porous enveloping member.

In some embodiments, the selective barrier(s) used is a membrane such as a reverse osmosis (RO) membrane, forward osmosis (FO) membrane or a Nano filtration (NF) membrane. Other additional selective barriers may be used for filtering larger particles in the stem fluid from penetrating into the compartment such as a rigid porous structure externally covering the membrane.

In specific embodiments, the osmoticum used in the detector is a water absorbent hydrogel such as PolyEthyleneGlycol (PEG).

In some embodiments, the pressure sensor of the water potential detector used is a piezoelectric transducer sensor, a strain gauge sensor or a combination thereof.

The method for measuring water potential in plants according to the invention is preferably, yet not necessarily, intended for plants having thick and solid stems such as trees and vines allowing drilling through their stem tissue using one or more drilling tools such as drillers without damaging their vascular conduit tissue.

In certain embodiments, the present invention provides a method for installing a water potential detector in a plant stem comprising the steps of: (a) providing a water potential detector of the invention as described herein; (b) forming a bore through the plant stem by drilling therein; (c) optionally, smoothening the inner walls of the bore; (d) inserting said water potential detector into the smoothened bore while placing a conductive gel in between the external surface of a selective barrier of the water potential detector and the stem tissue of the plant, such that there is no direct contact between said selective barrier and the stem tissue of the plant; (e) maintaining the stem tissue in the bore wet throughout the installation process; and (f) filling any remaining gaps between said water potential detector and the stem tissue with a fluid conducting material.

In certain embodiments, the present invention provides a method for installing a water potential detector in a plant stem comprising the steps of: (a) providing a water potential detector comprising: (i) a compartment with an osmoticum therein; (ii) at least one selective barrier for selective transfer of water between the plant tissue and the osmoticum, while blocking transfer of other ingredients within the plant fluid; (iii) a pressure sensor configured for sensing changes in pressure of said osmoticum in said compartment, wherein said water potential detector being configured for measuring water potential through intermediate contact with plant tissue adjacent to the vascular conduit of said plant stem via said at least one selective barrier; and (iv) optionally, a temperature sensor for measuring the temperature: inside the plant stem, of the sensor, or of the environment, or all; (b) forming a bore through the plant stem by drilling therein; (c) optionally, smoothening the inner walls of the bore; (d) inserting said water potential detector into the smoothened bore while placing a conductive gel in between said at least one selective barrier and the stem tissue of the plant, such that there is no direct contact between said at least one selective barrier and the stem tissue of the plant; (e) maintaining the stem tissue in the bore wet throughout the installation process; and (f) filling any remaining gaps between said water potential detector and the stem tissue with a fluid conducting material.

In certain detectors, it is essential that the selective barrier is maintained wet so that it won't ruin. Accordingly, in certain embodiments, the method of the invention further comprises maintaining said at least one selective barrier of said water potential detector wet throughout the delivery thereof to the plant site and throughout its installation in the plant stem. In specific embodiments, the method of the invention comprises a step of continuous injection of water through all its steps to thereby maintain said at least one selective barrier and the plant tissue in the stem wet.

In specific embodiments, to maintain the at least one selective barrier and the plant tissue wet throughout the installation process, one or more water injecting devices configured for continuous injection of water, are provided/used.

An exemplary process of the method of the invention is outlined in FIG. 3, comprising the steps of: (a) providing a water potential detector having a pressure sensor 11; (b) maintaining the one or more selective barrier of said water potential detector wet throughout the delivery thereof to the plant site and throughout its installation in the plant stem 12; (c) forming a bore through the plant stem 13; (d) (optional) smoothening the inner walls of said bore 14; (e) inserting the water potential detector into the bore while placing a conductive gel in between said at least one selective barrier and the stem tissue of the plant, such that there is no direct contact between said at least one selective barrier and the stem tissue of the plant 15; (f) filling gaps between the water potential detector and the stem tissue 16; (g) (optional) connecting each detector to a controller and operating thereof 17; and (h) (optional) fastening said water potential detector in place 18.

In certain embodiments, the step of forming a bore within the plant stem, and the smoothening the inner walls of the bore, are carried out by any suitable method and device, such as a drill, a grinder or a sander.

In certain embodiments of the method for installing a water potential detector in a plant stem according to the invention, said step (b) of forming a bore through the plant stem comprises the steps of: selecting a desired drilling location; attaching to the stem a drilling and fastening means that is designed to enable drilling at a specific angle and/or to a specific depth in the plant's stem, and following the drilling to fasten the sensor/detector inside the drilled bore.

Figure 7A:
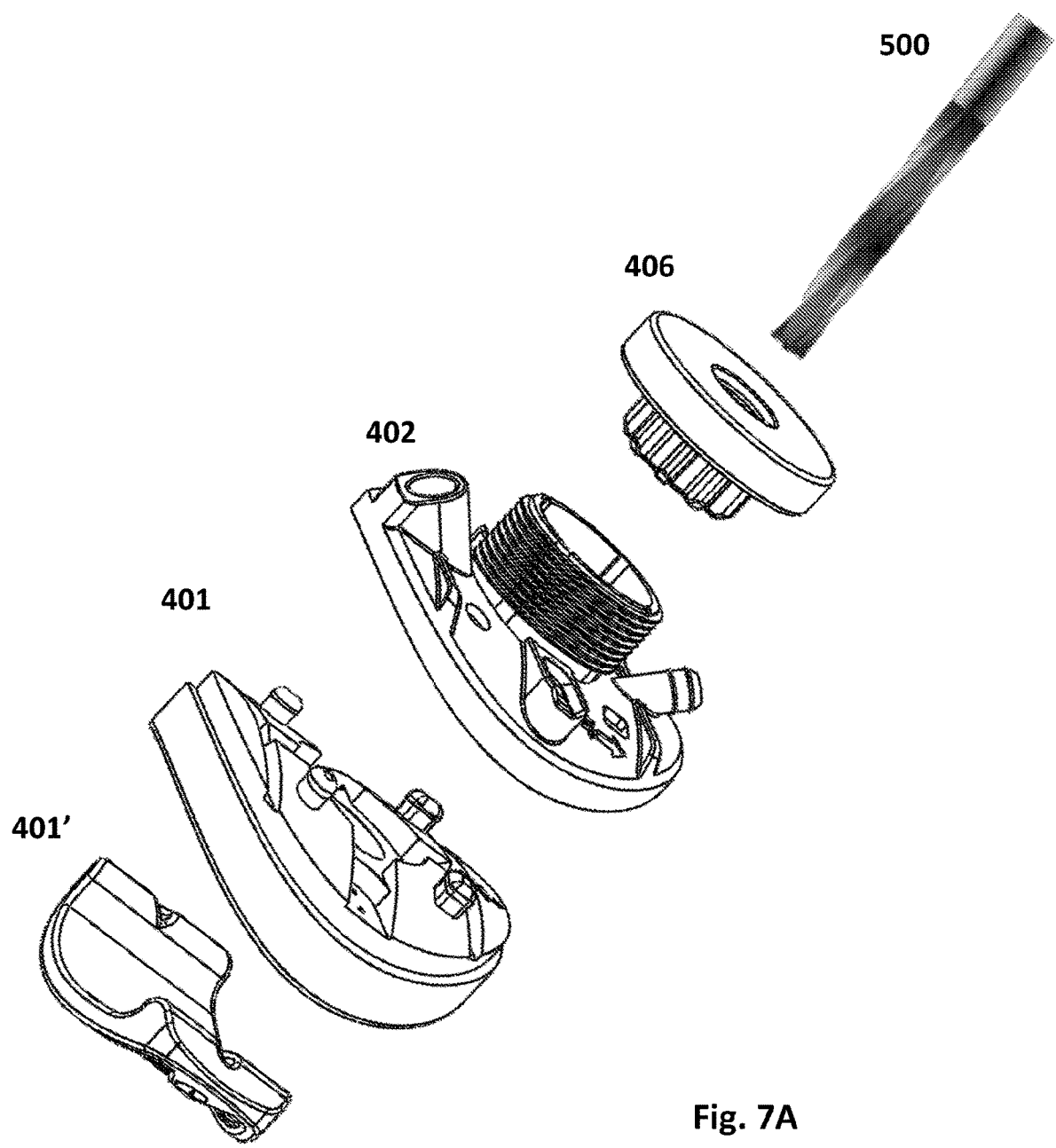
FIGS. 7A-7B are illustrations of the drilling process using the drilling and fastening means according to one embodiment of the invention.
Figure 7B:
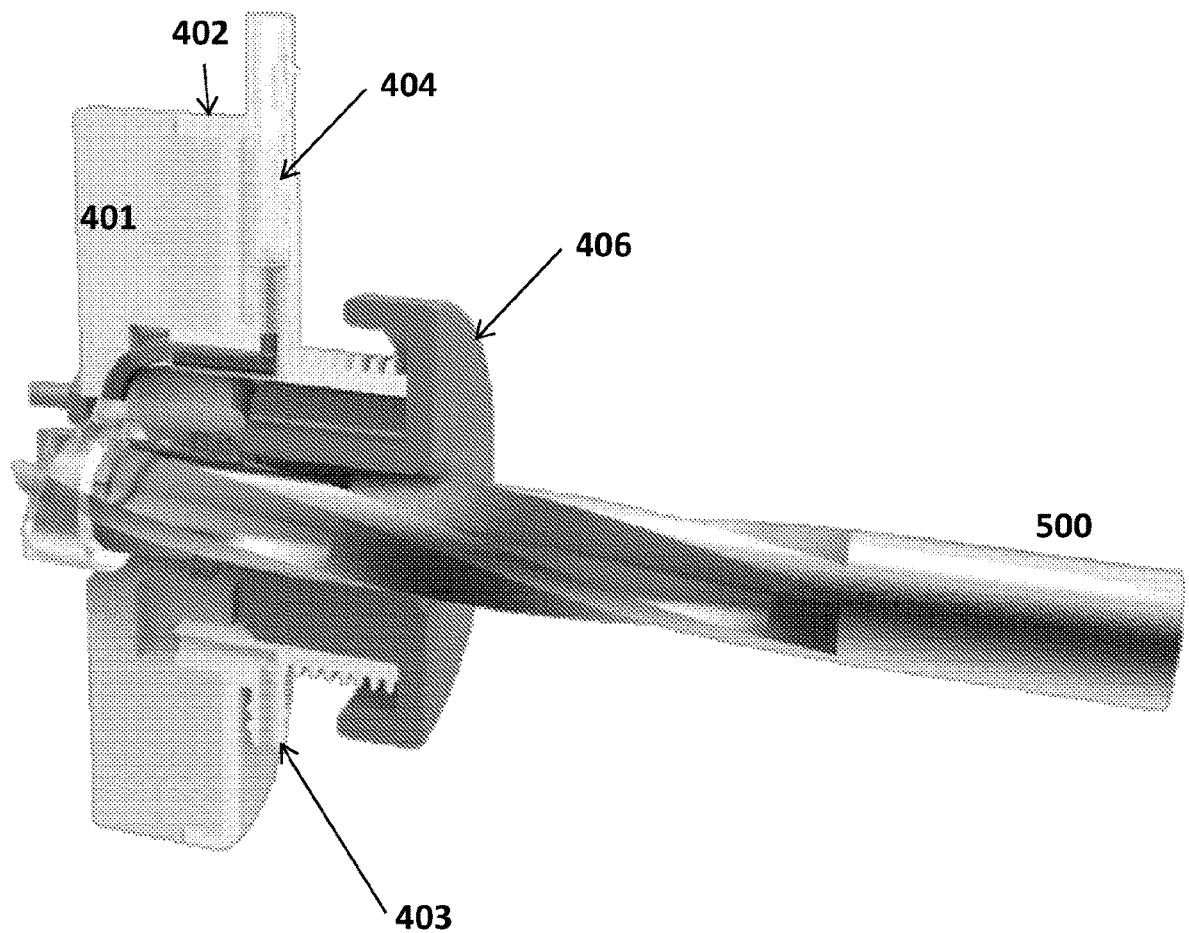

In specific embodiments, the drilling step comprises: (i) attaching to the stem a pad 401, optionally together with a rear brace 401' placed across the stem, e.g. in thin trunks or when trying to avoid drilling into the stem (i.e. the front panel 402 is fastened to the rear brace 401' while the tree stem is located in between them, thereby no damaging fastening means, such as screws or nails, are required). Alternatively, the pad 401 is attached directly to the stem, e.g., using screws or nails; (ii) assembling onto the pad 401 a cover unit/front panel 402 designed to enable attachment of a drill head 500 thereto, e.g. using a drill head lead/adaptor 406; and (iii) drilling. The above components are described in FIGS. 7A-7B. In certain embodiments, the pad 401 is made of rubber, silicon, plastic or any other suitable material that reduced damage to the tree that a rigid drilling and fastening means may cause. In specific embodiments, the pad 401 is not secured to the tree, but is used as a separating element between the front cover 402 and the tree to minimize possible damage to the tree by said cover 402.

In specific embodiments, the drilling step further comprises pumping/passing water or other cooling fluid into the drilled bore during the entire drilling process. This can be done via dedicated openings 403,404: one for allowing the insertion of fluid into the drilling site and the other allowing air and fluid to exit to thereby cool the drilling area as well as maintaining the bore wet throughout the entire drilling process and insertion of the sensor thereafter.

In certain embodiments, after the drilling has ended, the drilling head 500 and lead 406 are removed from the front panel 402—without dismantling the cover unit from the tree—and a detector 200 is inserted into the drilled bore, and is secured in place with a dedicated cork 405. In a specific embodiment, the detector 200 if further pushed into the bore using a dedicated external screw or an integral fastening/spring/push mechanism 407.

In specific embodiments, to maintain the plant tissue wet during the drilling process, said drilling and fastening means comprises a water/fluid inlet 403 through which water/gel can be passed into the drilled hole during drilling. In certain embodiments, said drilling and fastening means also comprises a water/fluid outlet 404 through which air and/or the water/gel can exit. In specific embodiments, said passing of fluid is also designed for cooling the stem and/or the drill during drilling.

Figure 8A:
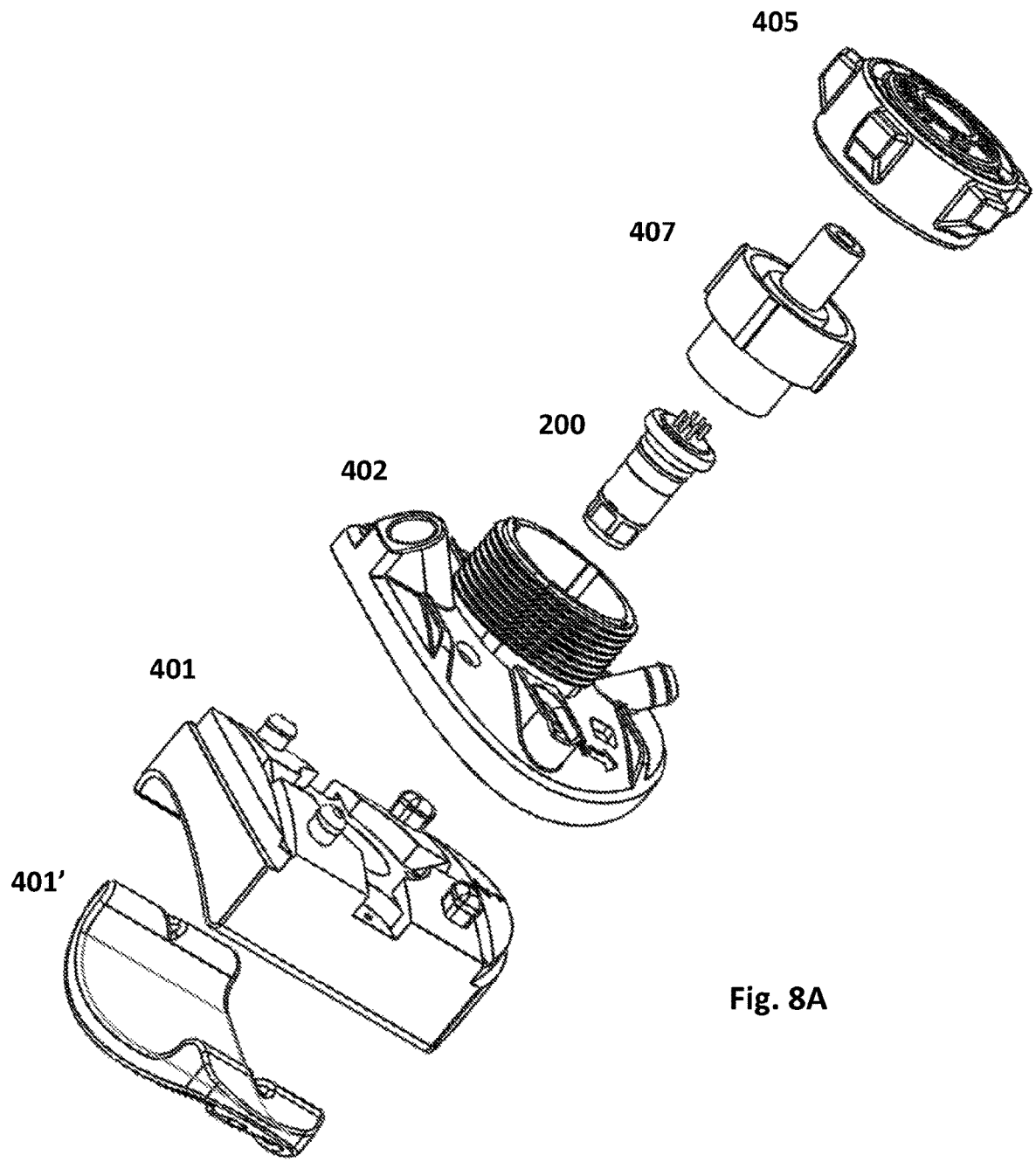
FIGS. 8A-8B are illustrations of the insertion and fixation of a sensor/detector of the invention using the drilling and fastening means according to one embodiment of the invention.
Figure 8B:
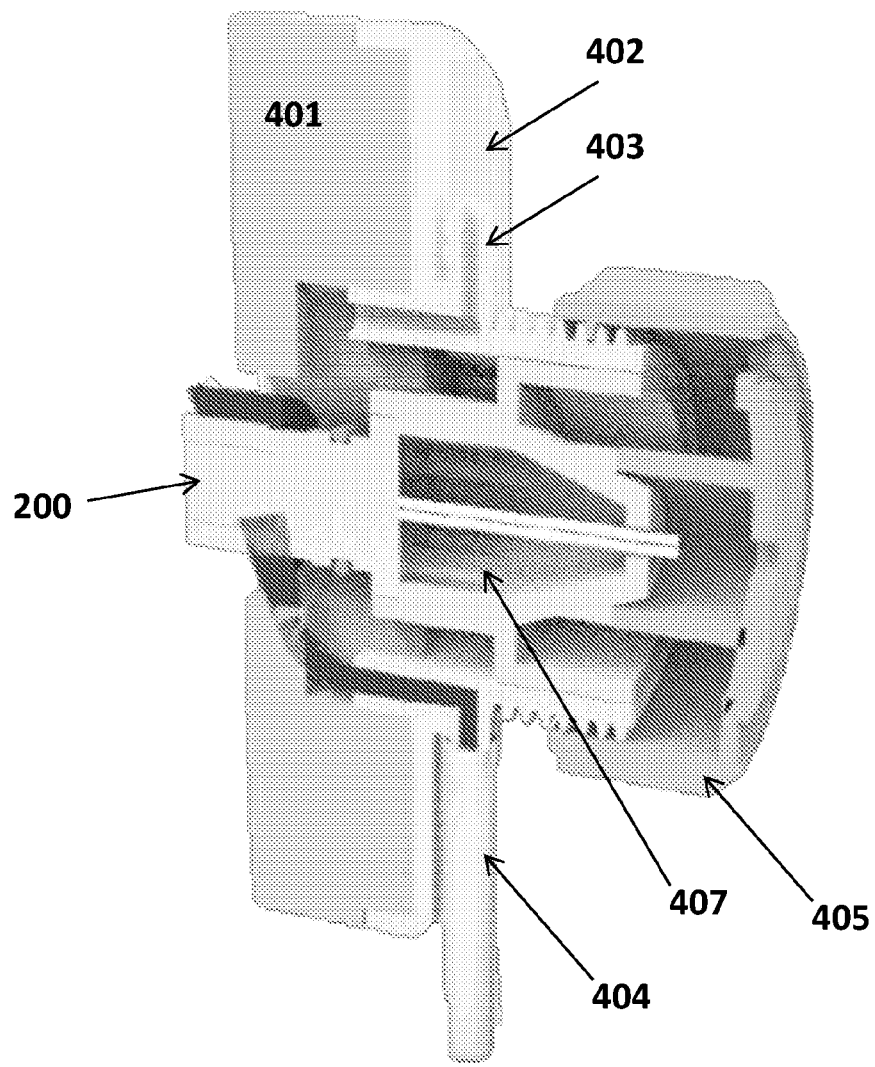

In yet other specific embodiments, to maintain the plant tissue and optionally also the detector's selective membrane wet during the insertion of the detector/sensor 200 into the bore and its fixation therein, water or other suitable fluid is pumped/passed through dedicated openings 403,404 in the front panel 402 (illustrated in FIG. 8B).

In certain embodiments, said dedicated openings 403,404 are used to insert a conductive gel into the bore between the stem and the detector's selective membrane maintain the plant tissue and optionally also the detector's external selective membrane to thereby prevent direct contact between said selective barrier and the stem tissue of the plant.

In a specific embodiment, the method of the invention further comprises a preliminary step of removing the bark, e.g. with a hole-punch, before forming said bore in step (b). This is done in order to make drilling easier, reduce damage to the plant, and reduce heating while drilling. Alternatively, the entire drilling step may be omitted and only a bark-removal step is performed, i.e. when it is sufficient to expose the plant inner tissue, e.g. as in plants with thin stems.

Figure 6D:
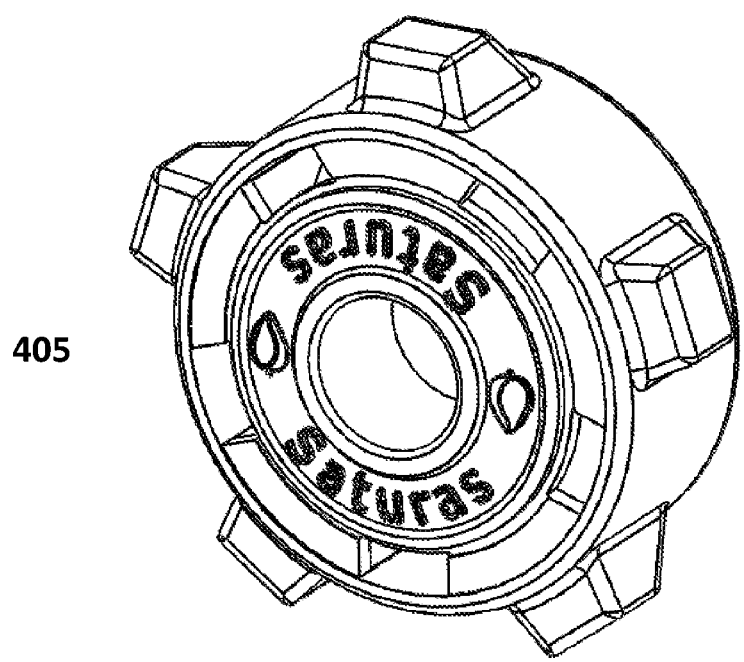
FIG. 6D is a fastening cork that is screed onto the cover unit/front panel.

According to some embodiments, the bore is drilled at a depth inside the plant stem that fits to the plant type and size such that the bore deepest edge is adjacent to the plant vascular conduit. In specific embodiments, in order to drill the bore at a depth and/or angle inside the plant stem that fits the plant type and size, the method of the invention comprises a step of using a drilling and fastening means as described hereinabove and in FIGS. 6-8.

In certain embodiments, the drilling aid 400 according to the invention enables to use a standard drilling head 500 for drilling the bore (as illustrated in FIG. 7).

In certain embodiments, a bore in the plant stem is formed in the stem (e.g. in the tree trunk) by drilling therein, using a first type of drill bit having a central spur and is configured for rough drilling to form the initial bore. In a specific embodiment, the bore is formed such that its deepest edge is adjacent to the vascular conduit (e.g. xylem) or to a depth that is proximate to the vascular conduit tissue (e.g. until reaching the xylem apoplast) of the stem for allowing the fluid transfer therefrom. Then, in certain embodiments, the inner walls of the initial bore that was formed are smoothened by using a second type of drill bit having for example smoothened edged wings. In specific embodiments, the drilling is done while constantly keeping the inner plant stem tissue wetted for wetting the bore that is formed while drilling thereof. In specific embodiments, the first type drill bit is a spiral bit having a spur and the second type drill bit is a spiral bit having no spurs or spindles. In yet another specific embodiment, said second type of drill bit is used to perform the smoothing for improving the intermediate contact between the selective barrier of the detector and the plant tissue for the fluid-to-fluid osmosis between the stem water and the osmoticum in the detector's compartment. This second drill bit may be designed as a spiral bit of bit having wings with smooth side surfaces having no spurs or recesses. Other types of drill bits can be used such as spiral bits one having a central spur and recesses thereover and the other with smoothened spiral head and no central spur.

In specific embodiments, the above steps of drilling with a first drill bit followed by a second drill bit, and optionally with a smoothening drilling bit, are carried out using the drilling and fastening means of the invention. Optionally, this is carried out by using a single drill head lead 406. Alternatively, this is carried out by using two or more different drill head leads 406, each suitable for a different drilling bit/head 500.

Sometimes, simply placing a detector in a drilled bore is insufficient, and there is a necessity to affix it in place. Accordingly, in certain embodiments, the method of the invention further comprises a step of fastening the water potential detector to the stem after step (f). In specific embodiment, said fastening is performed by using a dedicated fastening means, e.g. as that shown in FIGS. 1A-1B, and before sealing of the bore with a sealing material. In alternative specific embodiment, said fastening is performed by using a dedicated cork 405 that presses the sensor 200 against the stem. In yet another alternative specific embodiment, said fastening is performed by using dedicated fastening means 407 that is placed between the detector 200 and the cork 405.

FIGS. 1A and 1B show an exemplary fastening mean 100. After the bore is drilled and the detector is placed within the bore, the fastening mean 100 is secured over the detector, e.g. by screws or a belt, and a pressure-screw is then inserted therethrough via a dedicated hole 101 to push against the detector and prevent its movement. Notably, the securing of said fastening mean 100 to the stem does not injure the stem at the location of the drilled bore—if screws are used, they penetrate the stem on both sides of the bore and relatively remote therefrom, thereby reduce to a minimum potential damage to the stem at the bore location.

Figure 2A:
FIGS. 2A-2B are pictures showing a hole drilled into a plant's stem after removal of a fluid-potential measuring device.
Figure 2B:

Reference is now made to FIGS. 2A and 2B sowing a bore after a detector has been removed therefrom. FIG. 2A shows a bore in which the detector has been secured in place using standard technique, i.e. by using screws penetrating into the bore itself for holding the detector. As seen, the stem is markedly rotten and show advanced decaying. Contrary to that, FIG. 2B shows a bore in which the detector has been secured in place according to the method of the invention by using a securing mean with screws penetrating into the stem outside the bore area. As seen, the stem is completely healthy. Both bores were drilled at the same time, using the same technique, the same detector installed therein, and the detector remained in place for the same period of time.

In specific embodiments, the detector 200 of the invention comprises grooves, protrusions and/or screw-like engraving on its outer shell for facilitating fixation thereof in the drilled bore. In such a case, there is no immediate need to further fasten the detector in place. However, in certain embodiments, such a need arises in time, e.g., due to the growing of the plant or deteriorating of the bore walls. In such a case, fastening the detector can then be carried out.

Accordingly, in certain embodiments, the water potential detector used by the method of the invention comprises screw-like engravings on its exterior, and its insertion into the bore in step (d) is carried out by screwing it inside. In specific embodiments, said water potential detector further comprises a depth sensor indicating when it reached the bottom of the bore. Such depth sensor may be electronic or mechanic, e.g. a scale drawn on its outer wall.

In certain embodiments, the method of the invention further comprises connecting electronic leads in the installed water potential detector for communication therewith and controlling thereof. This is needed in case wired communication is used. However, it should be noted that the invention also encompass the usage of detectors with wireless communication capabilities, so that there is no need for such physical connection of electronic leads, and there is only a need for electronic communication between the detector and a remote control unit. Accordingly, in specific embodiments, the detector includes wireless based communication means such as RF communication means for wirelessly communicating with a remote control unit for transmitting sensor data thereto.

In certain embodiments, the fluid conducting material used for the filling of the gap between the detector and the stem tissue is, e.g., fluid conducting gel or caulking material or elastic silicone caulk.

In accordance with the present invention, any suitable water potential detector can be used. In specific embodiments, said water potential detector comprises a Micro Electro-Mechanical System (MEMS), which comprises said pressure sensor, a data processor, and a communication unit including a data transmitter, which is optionally wireless, and optionally also a receiver for communicating with a remote control device or system for transmitting thereto the measured potential data. The MEMS of the detector may require electronically connecting to output nodes thereof for communicating therewith.

The term "water potential detector" as used herein and throughout the application relates to passive sensing devices, which are controlled by a readout-communication device attached thereto. These detectors output relative resistance values of the pressure when excited by an external voltage supplied by said readout device, which further reads the changes of the response. In a specific embodiment of the present invention, said readout device constitutes said data transmitter.

In certain embodiments of the method of the invention, said placement of a conductive gel in between said at least one selective barrier and the stem tissue of the plant in step (d), is performed by filling the bore, at least partially, with said conductive gel in liquid form, and subsequently cross-link said liquid conductive gel into gel form, using any suitable device or method for said crosslinking. In a specific embodiment, said crosslinking is carried out immediately after filling the bore with the gel and prior to the insertion of said water potential detector into the bore. In an alternative specific embodiment, said crosslinking is carried out after the insertion of said water potential detector into the bore.

In alternative embodiments of the method of the invention, said placement of a conductive gel in between said at least one selective barrier and the stem tissue of the plant in step (d), is performed by: (i) placing an isolated disc, e.g. silicon, rubber, plastic, etc., comprising at least at the area in contact with said selective barrier a crosslinked conductive gel over said selective barrier; or (ii) placing a ring over said water potential detector such that the selective barrier remains exposed, covering said exposed selective barrier with said conductive gel in liquid form, and crosslinking said liquid conductive gel into gel form. In specific embodiments, said isolated disc in option (i) is made entirely of said crosslinked conductive gel. In other specific embodiments, said crosslinking is chemical, physical or electrical.

According to yet other specific embodiments, the present invention provides a method for measuring fluid potential in a plant tissue, said method comprising the steps of: (a) installing a water potential detector in a plant stem according to the method as described above, such that it creates hydraulic continuum with the plant tissue; (b) sensing changes in pressure caused due to osmosis based on flow of water into or out of said compartment caused to equilibrate the chemical potential of the plant tissue fluid and the osmoticum within the compartment; (c) sensing the temperature inside the plant tissue or the environment, or both; and (d) outputting electrical signal indicative of the sensed pressure, said changes are related to the fluid potential of the plant tissue with correlation to the environment temperature.

In specific embodiments of the above method, the step of sensing the temperature is carried out by a temperature sensor within said water potential detector. In an alternative embodiment, the step of sensing the temperature is carried out by a temperature sensor outside said water potential detector, e.g. implanted near the sensor, placed on top thereof, or placed nearby.

In certain embodiments, the above method further comprises the steps of: (i) receiving outputted data from said pressure sensor; (ii) optionally, transmitting data outputted by said pressure and temperature sensors to a processing unit, configured for conducting calculation of the fluid potential associated with the sensors output data; and (iii) calculating the fluid potential in said plant according to the sensed pressure and temperature at each given timeframe.

The present invention further provides systems for performing the above methods for measuring fluid potential and evaluating irrigation condition in a group of plants. Accordingly, the present invention provides a system for measuring fluid potential and evaluating irrigation condition in a group of plants, said system comprising: (a) a multiplicity of water potential detectors as defined above, each detector is to be inserted into a different plant of said group of plants according to any of the above methods; (b) at least one temperature sensor, either as part of said water potential detectors, or as an independent sensor, or both; and (c) a central unit configured for: (i) receiving sensor data from said pressure and temperature sensors within, optionally in real time, (ii) calculating the fluid potential of each plant in the group of plants based on data obtained from the sensors within said detectors, (iii) calculating the irrigation condition of each plant in the group of plants and/or of the entire group, according to the calculated fluid potential of each plant; and (iv) presenting the calculated fluid potential and/or irrigation condition of each plant and/or of the entire group of plants, and/or sending an alert to a user when the calculated irrigation condition exceeds predefined parameters.

In specific embodiments of the system of the invention, said central unit is further configured for transmitting data indicative of the evaluated irrigation condition of the group of plants to an irrigation system for controlling irrigation of the plants according to the evaluated irrigation condition thereof.

Accordingly, in certain embodiments, the central unit is configured for transmitting data indicative of the evaluated irrigation condition of the crop and/or irrigation recommendation plan based thereon to a separate irrigation system for controlling irrigation of the crop according to the evaluated irrigation condition thereof.

In some embodiments, multiple water potential detectors can be used to cover a large field area, each detector may be installed in a different plant of the crop at locations that are adapted to optimize measurements in relation to the number of water potential detectors and the size of the crop area and crop type.

In a specific embodiment, multiple water potential detectors can be used in a single plant, preferably a large branched plant, each detector installed in a different branch/stem of the plant to optimize measurements in said plant.

In specific embodiments, the central unit may include a computer having processing and communication means having a designated control application operable therethrough for carrying out the data communication and processing using at least one evaluation algorithm for the irrigation condition evaluation and calibration.

In certain embodiments, each water potential detector of the system comprises a compartment with an osmoticum and at least one selective barrier for measuring water potential in the plant stem in which it is installed via fluid osmosis, said at least one water potential detector being configured for communicating with said central unit via at least one communication link for transmitting data thereto indicative of the measured water potential. In specific embodiments, said water potential detector comprises one, two, three or more selective barriers.

In certain embodiments, each water potential detector also comprises a thermometer and is configured for transmitting temperature measurements to the central unit, e.g. to be used as reference data.

In certain embodiments, each water potential detector of the system of the invention further comprises a battery and a communication unit configured for wireless communication with the central unit. The communication unit is optionally adapted for radio frequency (RF) based communication. Alternatively, each detector is connected wirily to a power source, such as a solar panel or the main grid, optionally in parallel. In other alternative embodiments, each water potential detector comprises nodes for connecting to a communication unit for communicating with the central unit.

According to some embodiments of the invention, the water potential detector comprises multiple water potential detectors each installed in a different plant of the crop at locations that are adapted to optimize measurements in relation to the number of water potential detectors and the size of the crop area and crop type.

According to some embodiments of the invention, the central unit is a computer and communication device having a designated control application operable therethrough for carrying out the data processing using at least one evaluation algorithm for the irrigation condition evaluation and calibration.

In certain embodiments, once the bore is completed, the detector is placed therein while keeping the bore (inner stem tissue) and the detector's selective barrier(s) wet. Once positioned inside the bore, the bore is filled with fluid/gel conducting filling material and the detector is fastened to the stem using any fastening means known in the art that does not damage the tissue inside the bore.

In certain embodiments, the bore is filled with plant hormone(s) and/or growth substances, to assist and accelerate callus formation and callus growth at the sensor-tissue interface. This enables faster healing of the plant after insertion of the sensor/device, reduce potential damage to the plant, e.g. due to pathogens or pests, and aids in preventing rejection and removal of the sensor/device from the stem.

Plant hormone(s) and/or growth substances which can be used in accordance with the present method include, but are not limited to, abscisic acid; auxins; cytokinins; ethylene; gibberellins; brasinosteroids; salicylic acid; jasmonates; plant peptide hormones; polyamines; nitric oxide (NO); strigolactones; and karrikins.

Accordingly, in certain embodiments, the method according to the present invention comprises the steps of: (a) providing a water potential detector as described above configured for measuring water potential through intermediate contact with plant tissue adjacent to the vascular conduit of the plant stem; (b) maintaining said at least one selective barrier of said water potential detector wet throughout the delivery thereof to the plant site and throughout its installation in the plant stem; (c) removing the plant's bark; (d) forming a bore through the plant stem by drilling therein; (e) optionally, smoothening the inner walls of the bore; (f) inserting the water potential detector into the bore while placing a conductive gel in between said at least one selective barrier and the stem tissue of the plant, such that there is no direct contact between said at least one selective barrier and the stem tissue of the plant; (g) maintaining the stem tissue in the bore wet throughout the installation process; and (f) filling the gap between the water potential detector and the stem tissue with a fluid conducting material as well as plant hormone(s) and/or growth substances, wherein said plant hormone(s) and/or growth substances may be inserted into said smoothened bore before said potential detector is inserted therein.

In certain embodiments, step (d) of forming a bore through the plant stem by drilling therein, is carried out using a drilling and fastening means as described above. In yet another specific embodiment, step (e), if carried out, of smoothening the inner walls of the bore, is also carried out using the drilling and fastening means of the invention.

Once installed in the plant stem, the detector can be activated and optionally connected via wires or wirelessly to a control device that is capable of reading the output data from the sensor thereof.

According to other aspects, the present invention provides systems and methods for evaluating irrigation condition (e.g. water stress) in plant crops using one or more thermal imagery systems configured for thermal mapping of an area by also using one or more water potential detectors configured for measuring water potential in a plant stem for calibration of the data from the one or more thermal imagery systems. To evaluate the overall irrigation condition of the crop at each given timeframe a central unit is used. The central unit is configured for receiving thermal imaging data indicative of acquired crop temperature maps from the thermal imagery system(s), receiving data from the at least one water potential detector and for processing the received data for evaluating irrigation condition of the crop using the data from the at least one water potential detector reference at least for calibrating the data from the thermal imagery system.

In certain embodiments, the system of the invention includes several thermal imagery systems, e.g. ground based or airborne from low altitude flying platforms, for covering the entire crop field and water potential detectors installed in plant stems of the crop and configured for wirelessly transmitting signals indicative of its water potential and optionally also of its thermal measurements. Each thermal imagery system is positioned and configured for thermal mapping of an area of the crop field and transmitting data indicative thereof to a central unit, which is configured for receiving data from said water potential detectors and from said thermal imagery systems, and processing the received data to calculate the water stress in the crop or in areas thereof. In specific embodiments, the data from said water potential detectors is used at least for calibrating the crop water stress index (CWSI) of the thermal imagery systems. In specific embodiments, the thermal imagery systems include a thermal camera.

In certain embodiments, thermal maps of crop plots, irrigated as a distinct irrigation unit from a single valve, are used first place for selecting representative plants/trees for implanting therein water potential detectors. The selection is based on the average water stress of the irrigation unit, so the water stress transmitted for each sensor represents the average water stress of the plot as basis for decision how to irrigate the entire plot. This mode of plant/tree selection reduces the number of detectors needed considering spatial variability of the plants/trees in the field.

In another application of periodical thermal mapping according to the system and method of the invention, SWP-maps derived from thermal maps calibrated by SWP-sensors, serve both as extension of the sensor equipped plots to other sensor-less plots, and as control of the stress distribution within the plot, to thereby detect crop abnormalities, such as disease or pest damages, or irrigation malfunctions.

The data from the one or more water potential detectors, also referred to herein as "the reference data" provides the needed absolute ground stress or temperature reference for the calibration of the output of the thermal imagery systems. All other temperature levels can be related to pixel values of the imagery systems outputs even when using non-radiometric and therefore much less expensive thermal cameras for the imagery systems.

The water potential detector used for the calibration of the imagery system(s) output may be the detector described above, comprising a compartment with an osmoticum and at least one selective barrier for measuring water potential in the plant stem in which it is installed via fluid osmosis. The water potential detector may be configured for communicating with the central unit via at least one communication link for transmitting data thereto indicative of the measured water potential. This link may be wireless communication link e.g. using radio frequency (RF) communication technologies such as WiFi, ZigBee or any other wireless communication technology known in the art. Additionally or alternatively, the detector is configured for communication with the central unit via cabled communication for transmission of the reference data.

EXAMPLES

An Exemplary Assembling Process for a Pressure Sensor to a Tree (1) Before drilling into a tree, an appropriate pad 401 is selected according to the tree trunk. Such pad may be rubber, silicon or any other elastic material. Exemplary sizes of such a pad are 0-70 and 71-142 mm. In certain embodiments, e.g. when using the 0-70 mm pad, a rear brace 401' might also be needed to fasten the pad to the tree.

(2) Connecting the front panel 401 and optionally also the pad to the tree trunk with adequate screws.

(3) Attaching a water container to the water inlet 403 in the front panel 402 and verifying that the water runs through.

(4) Inserting/attaching a drill lead 406 into the front panel 402.

(5) Inserting a drill bit/head 500 into the drill lead 406 and adjusting a drill stopper to the correct depth.

(6) Drilling into the tree up to the stopper.

(7) Disassembling the drill lead 406 and inserting a sensor insert with a sensor 200.

(8) Closing the sensor insert with a locking ring/cork 405.

(9) Disassembling the water connector.

(10) Applying a sealing material such as room-temperature-vulcanizing (RTV) silicone to the bottom hole 404 in the front panel 402 until it exits from the upper water connector 403, thereby filling spaces between the sensor and stem.

Crosslinking PolyEthyleneGlycol (PEG)-DA Directly onto a Water Potential Detector As explained above, the present invention provides methods for measuring in real-time the water potential of a plant. In a specific embodiment, the method includes preliminary preparation of water-potential detectors before installation in a plant's stem. Accordingly, an example of such preliminary preparation comprises the following steps:

Preparing: (a) a PEG-DA solution in a concentration of about 20%; and (b) a photoinitiator (PI) solution (e.g. Irgacure 2959) in a concentration of about 10%;

Mixing the PEG solution with 1:100 PI solution;

Attaching/creating a ring blockade onto the water-potential detector at the selective barrier area;

Pouring said mixture into said ring blockade (which prevents spillage of the mixture); and Crosslinking the mixture for 5 min. using 365 nm UV light.

After the crosslinking step, the water potential detector comprises a layer/ring of conductive gel over its selective barrier, and is ready to be installed into a bore in a plant's stem. Then, for installation, the following steps are performed:

Drilling a bore in the stem while keeping the bore wet at all times, and filling the bore with water once drilling is done;

Inserting the water potential detector with its assembled conductive gel ring into the bore;

Sealing the contact area between the shell of the detector and the bore walls, e.g. with Sika-flex; and Affixing the detector to the bore with the fastening means according to the invention.

Figure 4A:
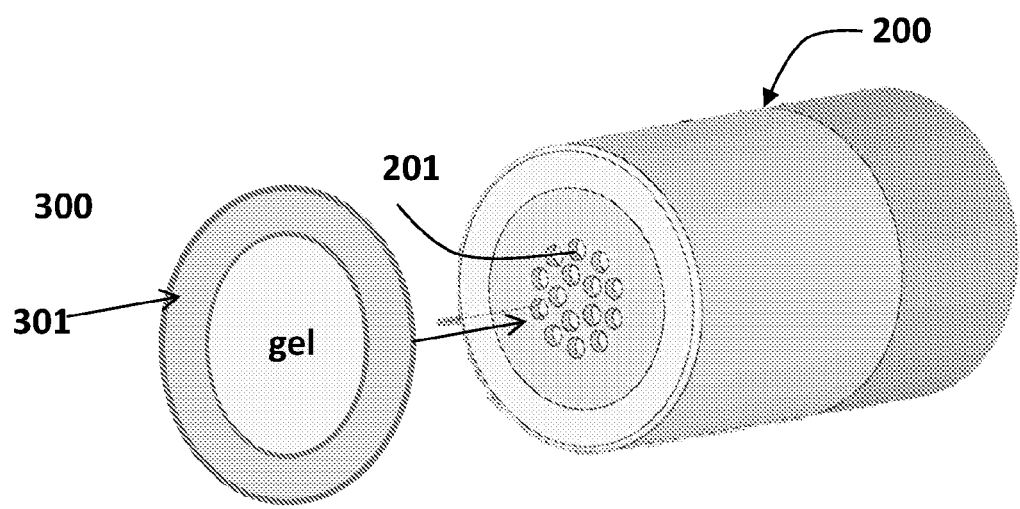
FIGS. 4A-4C are illustrations of a fluid-potential measuring device and a compatible isolating layer.

Creating a Crosslinked PEG Disk and Installing Same Together with a Water Potential Detector FIG. 4A illustrates an alternative embodiment for the above procedure, according to which, the conductive gel ring 300, optionally with an isolating ring 301, is first fabricated individually by any suitable means, e.g. as described above, but instead of pouring the mixture directly onto the detector, it is poured into disk-templates. After crosslinking of the gel in the template, the fabricated disks are removed from the templates and placed in between the selective barrier 201 of the detector 200 and the plant tissue in the drilled bore.

Figure 4B:
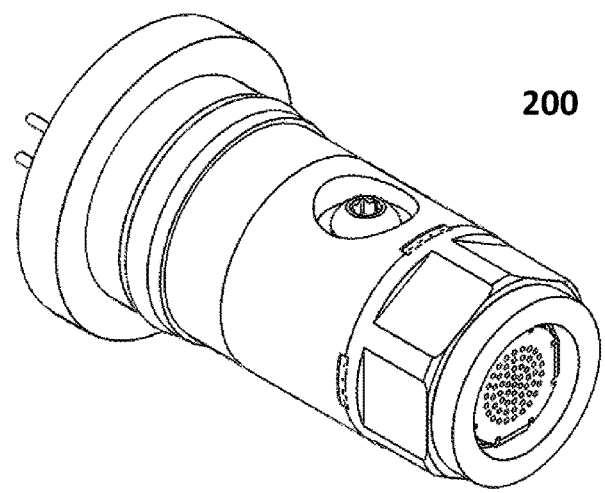
Figure 4C:
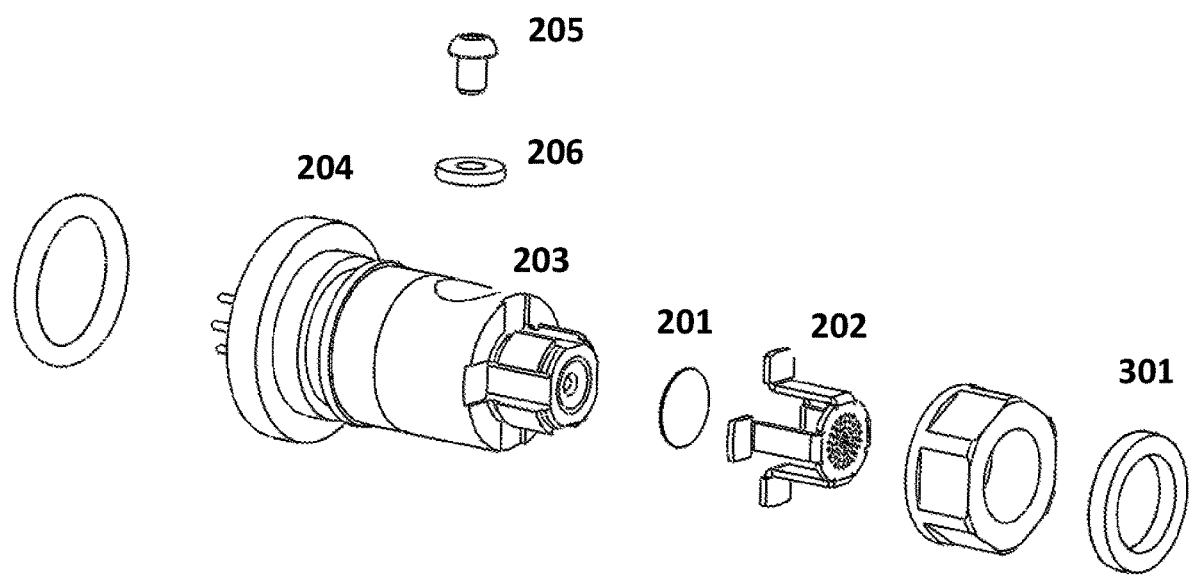

FIGS. 4B-4C illustrate an alternative embodiment for a detector/sensor 200 according to the invention: FIG. 4B illustrates the complete detector 200; and FIG. 4C is an exploded view thereof showing the detector's different components: the selective barrier 201; a rubber/silicon isolating ring for efficient adherence to the tree 301; a safety net 202 for the selective barrier; a compartment 203 with an osmoticum therein; a pressure sensor 204; and an osmoticum filling screw 205 and gasket 206.

Crosslinking PEG-DA During a Water Potential Detector Installation In-Situ

As explained above, the present invention provides methods for measuring in real-time the water potential of a plant. In a specific embodiment, the method does not include any preliminary preparations, and the addition of a conductive gel between each water-potential detector and the stem tissue is performed in-situ. Accordingly, an example of such procedure comprises the following steps:

Preparing: (a) a PEG-DA solution in a concentration of about 20%; an APS solution in a concentration of about 10%; and a TEMED solution in a concentration of about 10%;

Drilling a bore in the stem while keeping the bore wet at all times, and filling the bore with water once drilling is done;

Mixing the PEG-DA with 2% TEMED and 2% APS;

Drying the bore quickly, e.g. with an absorbent paper; and immediately pouring said mixture into the dried bore;

Inserting the water potential detector into the bore, optionally with an isolation ring, wherein the (chemical) crosslinking happens automatically within a few min.;

After the PEG is stabilized, sealing the contact area between the shell of the detector and the bore walls, e.g. with Sika-flex; and Affixing the detector to the bore with the fastening means according to the invention.

The Effect of Mediating Material on Stem Water Potential (SWP) Measurement

Figure 5:
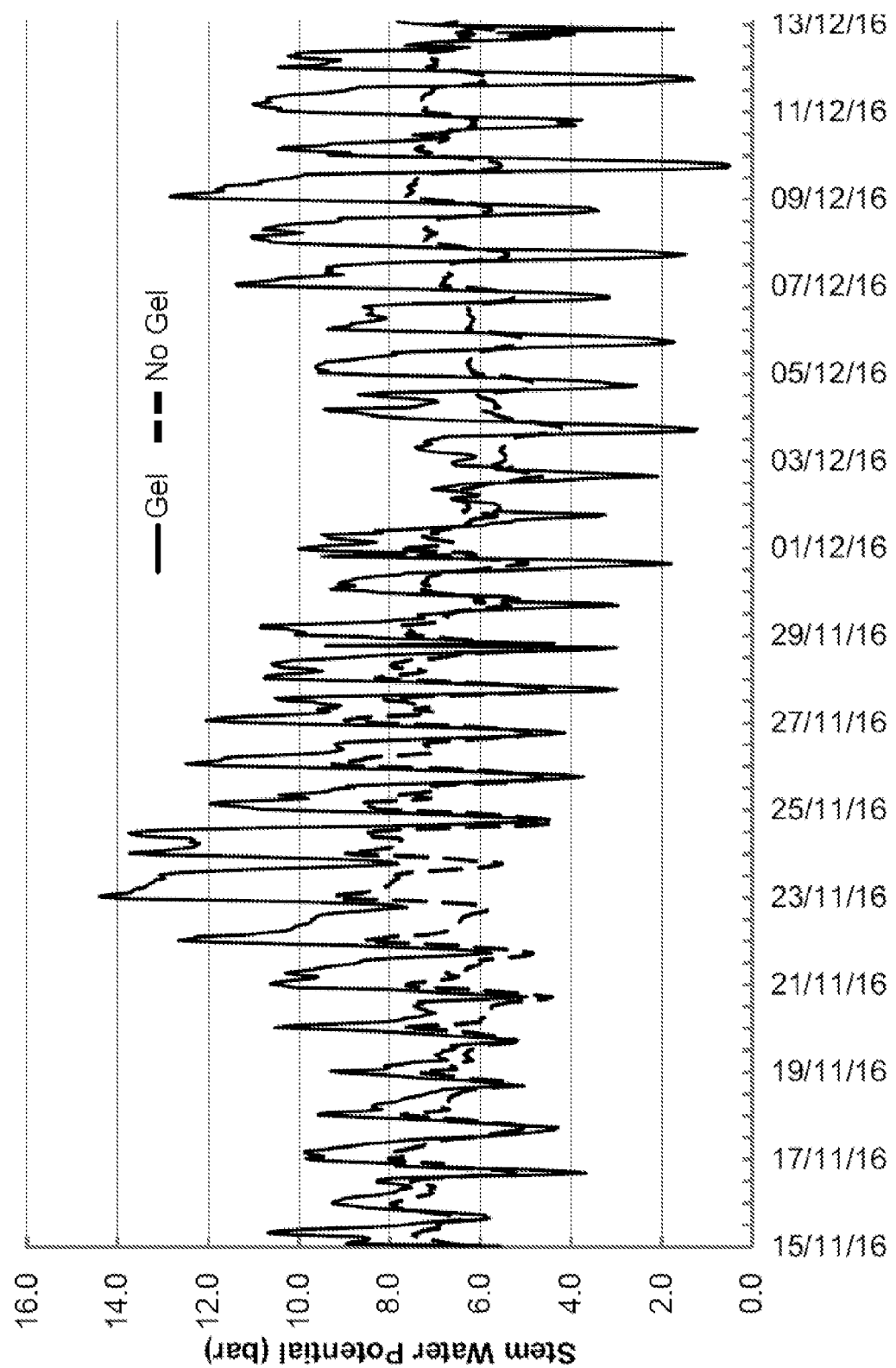
FIG. 5 is a graph showing the benefit of mediating material between the sensor and the stem. The amplitude of the sensor without any mediating material (dotted line) is low and finally the sensor is not responding at all.

FIG. 5 provides exemplary results of a single experiment, in which two identical sensors were installed in the same tree at the same time, using the same drilling technique and installed at the same height in the tree. One sensor was installed using mediating 20% PEG (solid line), whereas the other was installed without any mediating material (broken line).

In the first week the measurement trends of the two sensors were much a like although the second sensor amplitude was lower than the first one. As time passed, the amplitude of the second sensor has died out, while the measurement of the first sensor remained accurate and stable.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

The invention claimed is:

1. A method for installing a water potential detector in a plant stem comprising the steps of:
   a) providing a water potential detector;
   b) forming a bore through the plant stem by drilling therein;
   c) optionally, smoothening the inner walls of the bore;
   d) inserting said water potential detector into the smoothened bore while placing a conductive gel in between said detector and the stem tissue of the plant to prevent direct contact between the detector and the inner walls of the bore;

e) maintaining the stem tissue in the bore wet throughout the entire installation process; and f) filling any remaining gaps between said water potential detector and the stem tissue with a fluid conducting material, wherein said water potential detector comprises:

a compartment with an osmoticum therein;

at least one selective barrier for selective transfer of water between the plant tissue and the osmoticum, while blocking transfer of other ingredients within the plant fluid;

a pressure sensor configured for sensing changes in pressure of said osmoticum in said compartment, wherein said water potential detector being configured for measuring water potential through direct contact with plant tissue adjacent to the vascular conduit of said plant stem via said at least one selective barrier; and optionally, a temperature sensor for measuring the temperature: inside the plant stem, of the sensor, or of the environment, or all;

and wherein said conductive gel is placed in between said at least one selective barrier and the stem tissue of the plant, such that there is no direct contact between said at least one selective barrier and the stem tissue of the plant.

2. The method according to claim 1, further comprising at least one of the following steps: (i) removing the bark before forming said bore in step (b); (ii) continuous injection of water through all the steps of the method to thereby maintain said at least one selective barrier and the plant tissue in the stem wet; and (iii) filling gaps between the sensor and the stem with a sealing material.

3. The method according to claim 1, wherein the bore is drilled at a depth inside the plant stem that fits to the plant type and size such that the bore deepest edge is adjacent to the plant vascular conduit.

4. The method according to claim 1, wherein the bore is drilled with a dedicated drilling and fastening means for determining the drilling depth and/or angle.

5. The method according to claim 1, wherein said method further comprises a step of fastening the water potential detector to the stem, wherein said dedicated drilling and fastening means is optionally also for fastening of the water potential detector to the stem.

6. The method according to claim 1 further comprising a step of connecting electronic leads in the installed water potential detector for communication therewith and controlling thereof.

7. The method according to claim 1, wherein said water potential detector comprises a Micro Electro-Mechanical System (MEMS) comprising said pressure sensor, a data processor, and a data transmitter (optionally wireless).

8. The method according to claim 1, wherein said placement of a conductive gel in between said at least one selective barrier and the stem tissue of the plant in step (d), is performed by filling the bore, at least partially, with said conductive gel in liquid form, and subsequently crosslink said liquid conductive gel into gel form.

9. The method according to claim 8, wherein said crosslinking is carried out: (i) immediately after filling the bore with the gel and prior to the insertion of said water potential detector into the bore; or (ii) after the insertion of said water potential detector into the bore.

10. The method according to claim 1, wherein said placement of a conductive gel in between said at least one selective barrier and the stem tissue of the plant in step (d), is performed by: (i) placing an isolated disc comprising at least at the area in contact with said selective barrier a crosslinked conductive gel over said selective barrier; or (ii) placing a ring over said water potential detector such that the selective barrier remains exposed, covering said exposed selective barrier with said conductive gel in liquid form, and crosslinking said liquid conductive gel into gel form.

11. The method according to claim 10, wherein said isolated disc in option (i) is made entirely of said crosslinked conductive gel.

12. The method according to claim 8, wherein said crosslinking is chemical, physical or electrical.

13. The method according to claim 1, wherein said water potential detector comprises screw-like engravings on its exterior, and its insertion into the bore in step (d) is carried out by screwing it inside.

14. The method according claim 13, wherein said water potential detector further comprises a depth sensor indicating when it reached the bottom of the bore.

15. A method for measuring fluid potential in a plant tissue, said method comprising the steps of:

a) installing a water potential detector in a plant stem according to the method of claim 1, such that it creates hydraulic continuum with the plant tissue;

b) sensing changes in pressure caused due to osmosis based on flow of water into or out of said compartment caused to equilibrate the chemical potential of the plant tissue fluid and the osmoticum within the compartment;

c) sensing the temperature inside the plant tissue or the environment, or both; and d) outputting electrical signal indicative of the sensed pressure, said changes are related to the fluid potential of the plant tissue with correlation to the environment temperature.

16. The method according to claim 15, wherein the step of sensing the temperature is carried out by a temperature sensor within said water potential detector.

17. The method according to claim 15 further comprising the steps of:

a) receiving outputted data from said pressure sensor;

b) optionally, transmitting data outputted by said pressure and temperature sensors to a processing unit, configured for conducting calculation of the fluid potential associated with the sensors output data; and c) calculating the fluid potential in said plant according to the sensed pressure and temperature at each given timeframe.

18. A system for evaluating irrigation condition in crops using thermal imagery, said system comprising:

a) at least one thermal imagery system configured for thermal mapping of an area;

b) at least one water potential detector configured for measuring water potential in a plant stem in which it is installed and transmitting data indicative of its measurements, wherein each water potential detector is installed according to the method of claim 1; and c) a central unit configured for receiving thermal imaging data indicative of acquired crop temperature maps, receiving data from the at least one water potential detector and for processing the received data for evaluating irrigation condition of the crop using the data from the at least one water potential detector reference for calibrating the data from the thermal imagery system.

* * * * *